(12) United States Patent
Moon et al.

(10) Patent No.: US 9,494,543 B2
(45) Date of Patent: Nov. 15, 2016

(54) MEMS ELECTROCHEMICAL GAS SENSOR

(75) Inventors: Seung Eon Moon, Daejeon (KR); Nak Jin Choi, Daejeon (KR); Hyung Kun Lee, Daejeon (KR); Jae Woo Lee, Daejeon (KR); Woo Seok Yang, Daejeon (KR); Jong Dae Kim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 593 days.

(21) Appl. No.: 13/620,546

(22) Filed: Sep. 14, 2012

(65) Prior Publication Data

US 2013/0075255 A1    Mar. 28, 2013

(30) Foreign Application Priority Data

Sep. 28, 2011 (KR) .................. 10-2011-0098298

(51) Int. Cl.
*G01N 27/407* (2006.01)
*G01N 27/18* (2006.01)
*G01N 33/00* (2006.01)

(52) U.S. Cl.
CPC ............ *G01N 27/18* (2013.01); *G01N 33/004* (2013.01)

(58) Field of Classification Search
CPC ............ G01N 27/404–27/407; G01N 27/41; G01N 27/4045; G01N 27/4074
USPC ................ 204/410, 411, 421–429; 205/781, 205/783.5–785, 787; 73/23.31, 23.32
See application file for complete search history.

(56) References Cited

U.S. PATENT DOCUMENTS

| | | | | |
|---|---|---|---|---|
| 5,389,225 | A | * | 2/1995 | Aagard et al. ............... 204/426 |
| 2004/0026268 | A1 | * | 2/2004 | Maki et al. .................. 205/784 |
| 2005/0214170 | A1 | * | 9/2005 | Kading ........................ 422/88 |

FOREIGN PATENT DOCUMENTS

| | | |
|---|---|---|
| KR | 20-0351291 Y1 | 5/2004 |
| KR | 1020050032821 A | 4/2005 |
| KR | 1020090037062 A | 4/2009 |
| KR | 1020110066849 A | 6/2011 |

OTHER PUBLICATIONS

Tao et al. Sensors and Acutators B, 81, 2002 237-247.*
Liu et al. The Electrochemical Society Interface, 2004, 22-27.*
J. F. Currie et al., "Micromachined thin film solid state electrochemical $CO_2$, $NO^2$ and $SO_2$ gas sensors", Sensors and Actuators B Chemical, 1999, pp. 235-241, vol. 59, Elsevier.

* cited by examiner

*Primary Examiner* — Gurpreet Kaur

(57) ABSTRACT

Disclosed is an electrochemical gas sensor using micro electro mechanical systems (MEMS). The MEMS electrochemical gas sensor includes: a substrate a lower central region of which is etched by a predetermined thickness; a first insulation film formed on the substrate; a heat emitting resistance body formed on the first insulation film; a second insulation film formed on the heat emitting resistance body; a reference electrode formed in an upper central region of the second insulation film; a solid electrolyte formed on the reference electrode; and a detection electrode formed on the solid electrolyte.

13 Claims, 4 Drawing Sheets

MEMS ELECTROCHEMICAL GAS SENSOR

CROSS-REFERENCE TO RELATED APPLICATIONS

This application is based on and claims priority from Korean Patent Application No. 10-2011-0098298, filed on Sep. 28, 2011, with the Korean Intellectual Property Office, the disclosure of which is incorporated herein in its entirety by reference.

TECHNICAL FIELD

The present disclosure relates to an electrochemical gas sensor, and more particularly, to an electrochemical gas sensor using micro electro mechanical systems (MEMS).

BACKGROUND

A representative gas detected by an electrochemical gas sensor includes $CO_2$. $CO_2$ gas is harmless and is an element inevitable for photosynthesis of plants, but an amount of CO2 has increased continually along with the development of the civilization, causing environmental problems such as global warming or abnormal climate due to the green house effect. Accordingly, $CO_2$ gas sensors for regulating carbon credits in the industrial field or exhaust gases of vehicles are being increasingly demanded.

Meanwhile, currently, optical gas sensors using non-dispersive infrared absorption (NDIR) are being mainly used as $CO_2$ gas sensors. While the optical gas sensors can realize an accurate measurement, have a long life span, and show stability, they cannot be easily used as a general sensor due to their high prices and may cause errors in a humid environment.

Studies on potentiometric electrochemical gas sensors are being actively made using solid ionic conductors (solid electrolyte) as sensors capable of overcoming the disadvantage of the optical gas sensors. An electrochemical gas sensor has a simple structure, shows an excellent gas selectivity, and allows a detection of a gas having low concentration of a ppm level. In addition, since electrochemical gas sensors can be manufactured at a low price as compared with the optical gas sensors, there is a high possibility of using the electrochemical gas sensors as a distributed gas analyzer or a general sensor available for homes or offices.

Meanwhile, methods of manufacturing gas electrochemical gas sensors according to the related art include a method of depositing a detection electrode and a reference electrode on one surface of a solid electrolyte ceramic and depositing a high temperature heater for an operation of the sensor on an opposite surface thereof, and a method of stacking a solid electrolyte thick film, a detection electrode, and a reference electrode on one surface of a substrate formed of alumina or quartz and depositing a sensor operating heater on an opposite surface thereof to manufacture an electrochemical gas sensor.

Since the bulk electrochemical gas sensors are resistant to a sudden impact, but require high power consumption and a big size to maintain a high temperature for an operation of the sensor, It is difficult to apply the bulk electrochemical gas sensors to portable terminals or ubiquitous sensor network (USN) sensor nodes.

Accordingly, in order to allow an electrochemical gas sensor to be mounted to a portable terminal, a USN sensor network or the like as a general sensor, a MEMS electrochemical gas sensor needs to consume little power, have a small size, and be mass-produced.

The present disclosure has been made in an effort to provide a MEMS electrochemical gas sensor which has an ultra small size and significantly reduces power consumption.

The present disclosure also has been made in an effort to provide an MEMS electrochemical gas sensor which provides services in various environments.

An exemplary embodiment of the present disclosure provides a MEMS electrochemical gas sensor, including: a substrate a lower central region of which is etched by a predetermined thickness; a first insulation film formed on the substrate; a heat emitting resistance body formed on the first insulation film; a second insulation film formed on the heat emitting resistance body; a reference electrode formed in an upper central region of the second insulation film; a solid electrolyte formed on the reference electrode; and a detection electrode formed on the solid electrolyte.

Another exemplary embodiment of the present disclosure provides a MEMS electrochemical gas sensor, including: a substrate a lower central region of which is etched by a predetermined thickness; a first insulation film formed on the substrate; a heat emitting resistance body formed on the first insulation film; a second insulation film formed on the heat emitting resistance body; a solid electrolyte formed in an upper central region of the second insulation film; a reference electrode formed at one side of an upper portion of the solid electrolyte; and a detection electrode formed at an opposite side of the upper portion of the solid electrolyte.

According to the exemplary embodiments of the present disclosure, power consumption is reduced, as compared with an existing bulk electrochemical gas sensor, by providing an MEMS electrochemical gas sensor where a substrate is etched by a predetermined thickness to thermally isolate insulation films and a heat emitting resistance body.

Further, signal processing/transmitting circuits can be integrated on a substrate by using a semiconductor process and accordingly can be mounted to various systems (for example, a portable terminal, a sensor node or the like) while realizing various services in an extreme environment, by providing a MEMS electrochemical gas sensor having a vertical detection electrode/solid electrolyte/reference electrode structure.

In addition, a MEMS electrochemical gas sensor having low-power characteristics can be used for a long period of time even within a restricted battery capacity, and can be stably driven by using a self-charged power source in various environments where energy converting elements such as a thermoelectric element, a piezoelectric element and the like are operated.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which form a part hereof. The illustrative embodiments described in the detailed description, drawing, and claims are not meant to be limiting. Other embodiments may be utilized, and other changes may be made, without departing from the spirit or scope of the subject matter presented here.

Hereinafter, exemplary embodiments of the present disclosure will be described in detail with reference to the accompanying drawings. In a description of the present disclosure, a detailed description of related known configurations and functions will be omitted when it may make the essence of the present disclosure obscure.

Figure 1:
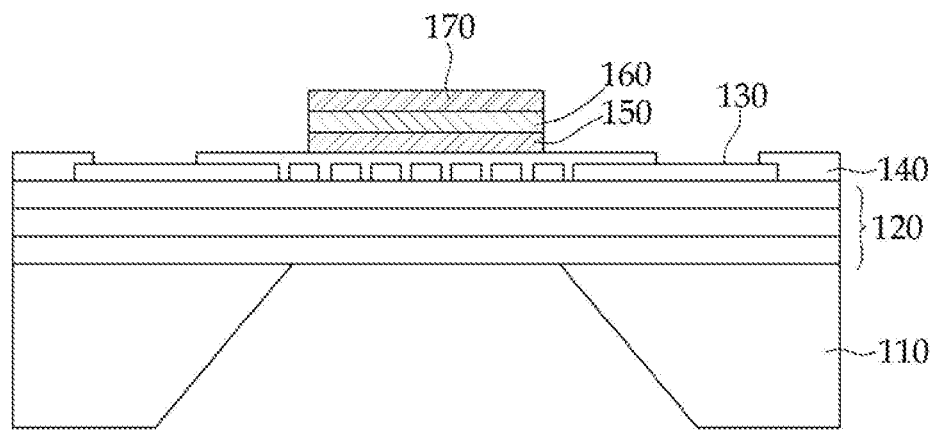
FIG. 1 is a sectional view illustrating a MEMS electrochemical gas sensor according to an exemplary embodiment of the present disclosure.

FIG. 1 is a sectional view illustrating a MEMS electrochemical gas sensor according to an exemplary embodiment of the present disclosure.

Referring to FIG. 1, the MEMS electrochemical gas sensor according to the exemplary embodiment of the present disclosure includes a substrate 110, a first insulation film 120 formed on the substrate 110, a heat emitting resistance body 130 formed on the first insulation film 120, a second insulation film 140 formed on the heat emitting resistance body 130, a reference electrode 150 formed in an upper central region of the second insulation film 140, a solid electrolyte 160 formed on the reference electrode 150, and a detection electrode 170 formed on the solid electrolyte 160. The MEMS electrochemical gas sensor according to the present disclosure may further include an attachment layer (not shown) using chrome (Cr) or titanium (Ti) between the first insulation film 120 and the heat emitting resistance body 130 to further increase bonding force when the heat emitting resistance body 130 is formed.

A lower central region of the substrate 110 is etched by a predetermined thickness to thermally isolate the first insulation film 120 and the heat emitting resistance body 130. Here, the substrate 110 may be a silicon substrate used in a general semiconductor process, or may be a substrate doped with aluminum oxide ($Al_2O_3$), magnesium oxide (MgO), quartz, gallium-nitrogen (GaN) or gallium-arsenic (GaAs).

The first insulation film 120 may include a single or plurality of silicon oxide films or silicon nitride films, and serves to structurally support the heat emitting resistance body 130 and protect the heat emitting resistance body 130 when the substrate 110 is etched.

The heat emitting resistance body 130 serves to increase a ambient temperature to improve gas detection characteristics. Here, the heat emitting resistance body 130 may be formed of a metal such as platinum (Pt), palladium (Pd), iridium (Ir), tungsten (W) or gold (Au), silicon or a conductive metal oxide and may be formed with various shapes having lines.

The second insulation film 140 includes a single or plurality of silicon oxide films or silicon nitride films, and is located between the heat emitting resistance body 130 and the reference electrode 150 to electrically insulate the heat emitting resistance body 130 and the reference electrode 150. The second insulation film 140 is etched such that a portion of the heat emitting resistance body 130 is exposed. Thus, the heat emitting resistance body 130 may be connected to an external circuit through a heater electrode pad (not shown) and a bonding wire (not shown).

Figure 2:
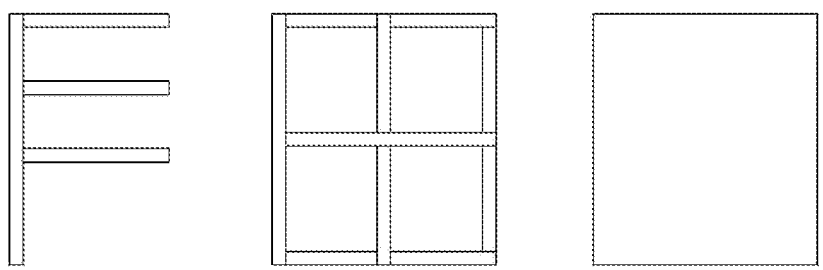
FIG. 2 is a view illustrating various shapes of a reference electrode and a detection electrode of the MEMS electrochemical gas sensor according to the exemplary embodiment of the present disclosure.

The reference electrode 150 may be formed of at least one material reactionless to a gas to be detected, and may be formed of a metal such as platinum (Pt), palladium (Pd), iridium (Ir), tungsten (W) or gold (Au) and an oxide material such as $Ag_2SO_4$, $Na_2Ti_6O_{13}$—$TiO_2$, $Li_2TiO_3$—$TiO_2$, $LiMn_2O_4$, $LiCoO_2$—$Co_3O_4$ and $Na_2ZrO_3$—$ZrO_3$ according to the kind of the solid electrolyte 160. Here, as illustrated in FIG. 2, the reference electrode 150 may be formed in the form of an interdigital shape, a hollow box shape or a box shape, or a combination thereof. Bonding wires (not shown) for transferring signals may contact both ends of the reference electrode 150.

The solid electrolyte 160, which is a both insulating and electrically conductive material and is a material, shows an electric conductivity when ions flow in a solid at a rapid speed of approximately $10^{-6}$ to $10^{-2}$ $\Omega^{-1}$ $cm^{-1}$. Positive ions such as $Ag^+$, $Cu^+$, $Na^+$, $Li^+$, $K^+$ and $H^+$ or negative ions such as $O^{2-}$, $F^-$, $Cl^-$ and $I^-$ may flow through the solid electrolyte 160, and the solid electrolyte 160 may include YSZ(Yttria Stabilized Zirconia), $K_2CO_3$, NASICON($Na_{1+x}Zr_2Si_xP_{3-x}O_{12}$), $\beta$-$Al_2O_3$($Na_2O.11Al_2O_3$), $Li_3PO_4$, LISICON ($Li_{2+2x}Zn_{1-x}GeO_4$), LIPON(Lithium Phosphorous Oxynitride), $Li_2CO_3$—MgO, $Li_2SO_4$, $Li_4SiO_4$, $Li_{14}ZnGe_4O_{16}$, $\gamma$-$Li_{3.6}Ge_{0.6}V_{0.4}O_4$, $Li_3N$, Li-$\beta$-alumina, $Li_{1-x}Ti_{2-x}Mx(PO_4)_3$(M=Al, Sc, Y or La), LGPS($Li_2GeP_2S_{12}$) and $Li_xLa_{(2-x)/3}TiO_3$ for detection of carbon dioxide.

The detection electrode 170 may be formed of at least one material causing a change in electromotive force by a reaction with a gas to be detected, and may be formed of a metal such as platinum (Pt), palladium (Pd), iridium (Ir), tungsten (W) or gold (Au) and an oxide material such as $Na_2CO_3$ or mixed $Na_2CO_3$($Na_2CO_3$—$BaCO_3$, $Na_2CO_3$—$Li_2CO_3$, $Li_2CO_3$—$BaCO_3$, $Li_2CO_3$—$CaCO_3$ and the like), $Li_2CO_3$ or mixed $Li_2CO_3$($Li_2CO_3$—$BaCO_3$, $Li_2CO_3$—$SrCO_3$, $Li_2CO_3$—$CaCO_3$ and the like) according to the kind of the solid electrolyte. Here, the detection electrode 170 may be formed in the form of an interdigital shape, a hollow box shape or a box shape, or a combination thereof like the reference electrode 150. Bonding wires (not shown) for transferring signals may contact both ends of the detection electrode 170.

Figure 3:
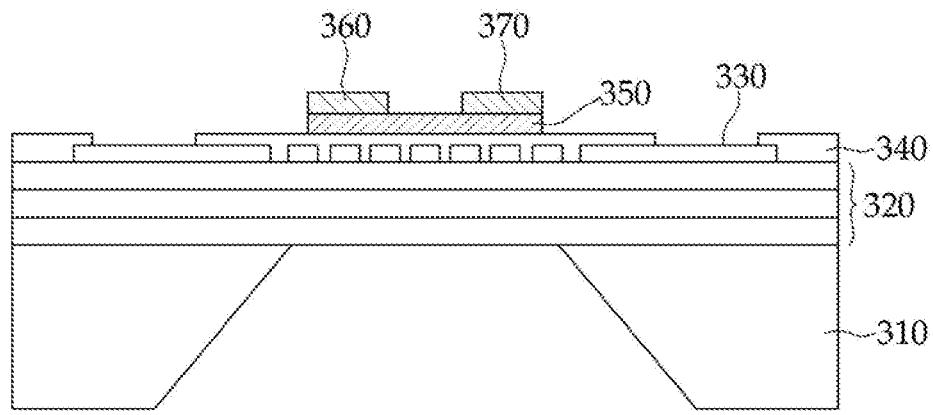
FIG. 3 is a sectional view illustrating a MEMS electrochemical gas sensor according to another exemplary embodiment of the present disclosure.

FIG. 3 is a sectional view illustrating a MEMS electrochemical gas sensor according to another exemplary embodiment of the present disclosure.

Referring to FIG. 3, like the MEMS electrochemical gas sensor of FIG. 1, the MEMS electrochemical gas sensor according to the another exemplary embodiment of the present disclosure includes a substrate 310, a first insulation film 320, a heat emitting resistance body 330, a second insulation film 340, a solid electrolyte 350, a reference electrode 360, a detection electrode 370 and the like.

However, unlike the MEMS electrochemical gas sensor of FIG. 1, the MEMS electrochemical gas sensor according to another exemplary embodiment of the present disclosure has a structure where the reference electrode 360, the solid electrolyte 350 and the detection electrode 370 are horizontal. In detail, the reference electrode 360 is formed at one side of an upper portion of the solid electrolyte 350, and the detection electrode 370 is formed at an opposite side of the upper portion of the solid electrolyte 350.

Thus, while the MEMS electrochemical gas sensor according to the another exemplary embodiment of the present disclosure can minimize power consumption like the MEMS electrochemical gas sensor of FIG. 1, the MEMS electrochemical gas sensor deteriorates degree of integration as compared with the MEMS electrochemical gas sensor of FIG. 1.

Figure 4:
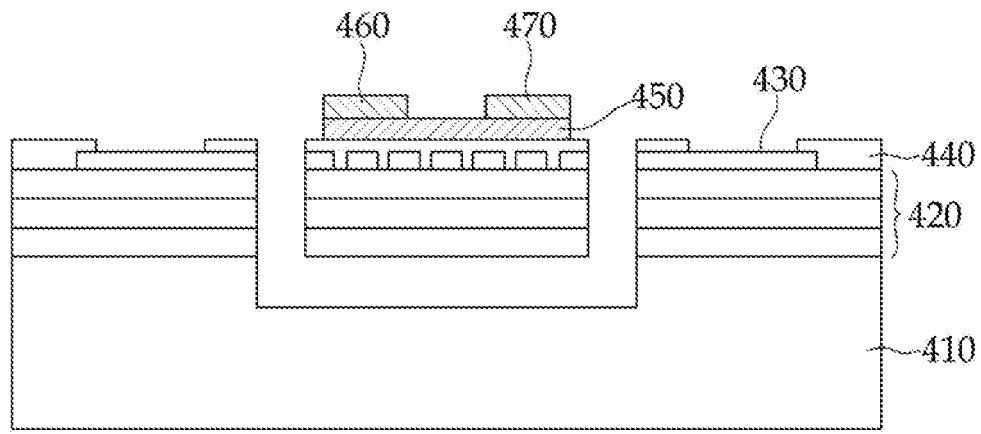
FIGS. 4 and 5 are sectional views of MEMS electrochemical gas sensors according to other exemplary embodiments of the present disclosure.
Figure 5:
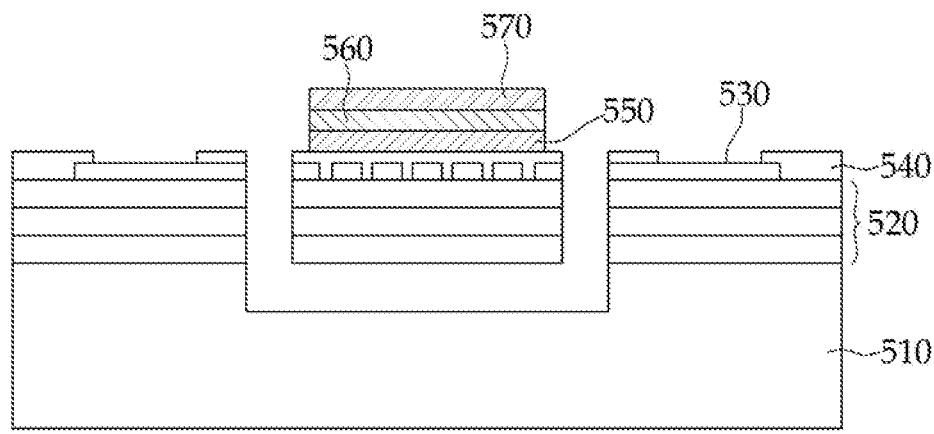

FIGS. 4 and 5 are sectional views of MEMS electrochemical gas sensors according to other exemplary embodiments of the present disclosure.

Referring to FIGS. 4 and 5, like the MEMS electrochemical gas sensor of FIG. 3, the MEMS electrochemical gas sensors according to the other exemplary embodiments of the present disclosure include substrates 410 and 510, first insulation films 420 and 520, heat emitting resistance bodies 430 and 530, second insulation films 440 and 540, solid electrolytes 450 and 560, reference electrodes 460 and 550, detection electrodes 470 and 570 and the like.

However, unlike the MEMS electrochemical gas sensor of FIG. 3, in the MEMS electrochemical gas sensors according to the other exemplary embodiments of the present disclosure, upper central regions of the substrates 410 and 510 are etched by a predetermined thickness to thermally isolate the first insulation films 420 and 520 and the heat emitting resistance bodies 430 and 530. To this end, the upper central regions of the substrates 410 and 510 are etched through surface-micromachining.

Thus, like the MEMS electrochemical gas sensors of FIGS. 1 and 3, the MEMS electrochemical gas sensors according to the other exemplary embodiments of the present disclosure can minimize power consumption and can be easily manufactured or treated as well because rear surfaces of the substrates are closed.

FIGS. 6A to 6G are process flowcharts illustrating a method of manufacturing a MEMS electrochemical gas sensor according to an exemplary embodiment of the present disclosure.

Figure 6A:
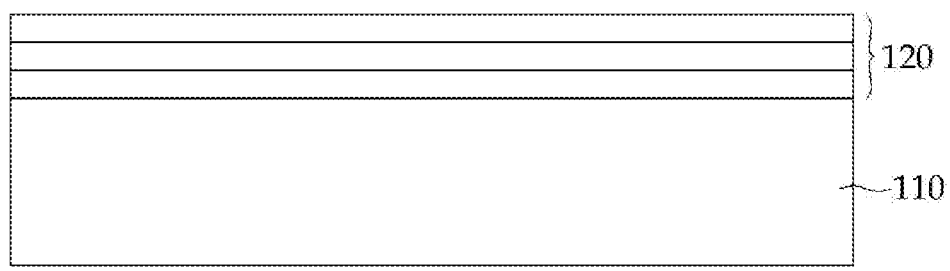
FIGS. 6A to 6G are process flowcharts illustrating a method of manufacturing a MEMS electrochemical gas sensor according to an exemplary embodiment of the present disclosure.

Referring to FIG. 6A, the first insulation film 120 is formed by depositing a single or plurality of silicon oxide films or silicon nitride films on the substrate 110 through a deposition process such as thermal deposition, sputtering deposition, chemical vapor deposition or the like.

Figure 6B:
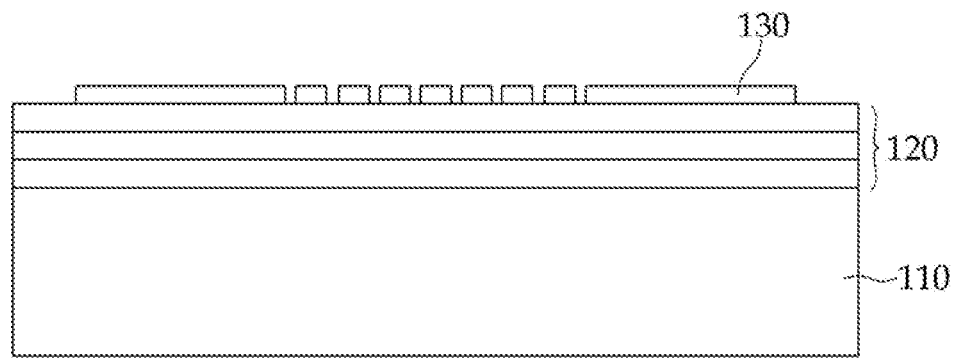

Referring to FIG. 6B, the heat emitting resistance body 130 is formed by depositing a metal film such as platinum (Pt), palladium (Pd), iridium (Ir), tungsten (W), or gold (Au), a silicon film, a conductive metal oxide film or the like on the first insulation film 120 through a deposition process such sputtering deposition, electronic beam deposition, vapor deposition or the like.

Figure 6C:
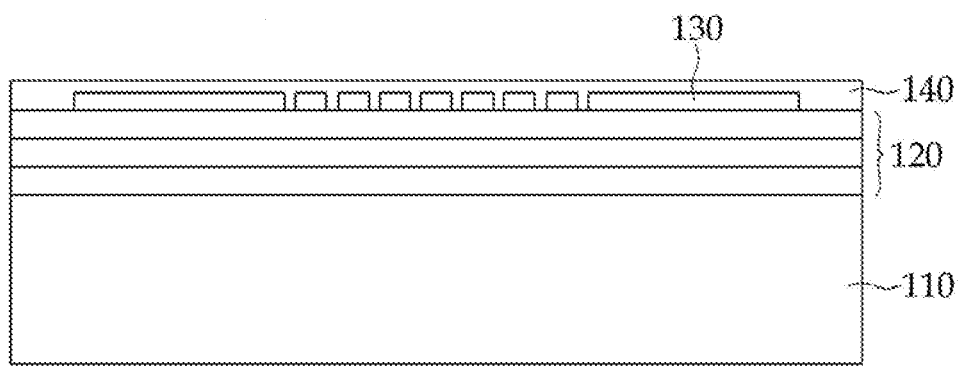

Referring to FIG. 6C, the second insulation film 140 is formed by depositing a single or plurality of silicon oxide films or silicon nitride films on the heat emitting resistance body 130 through a deposition process such as thermal oxidation deposition, sputtering deposition, chemical vapor deposition or the like.

Figure 6D:
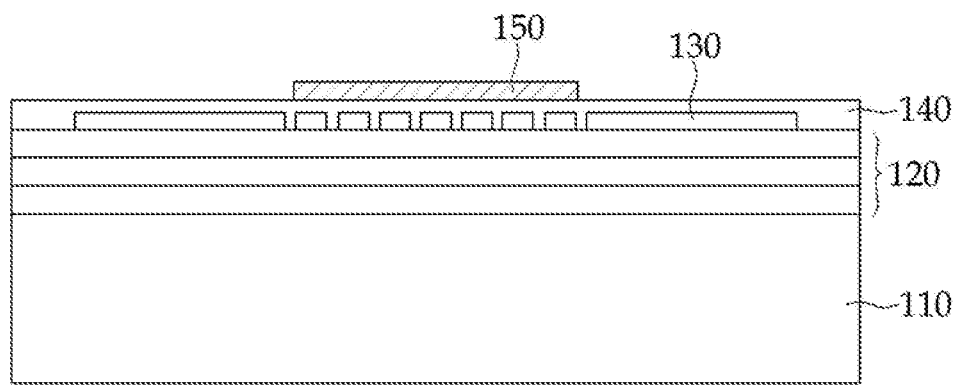

Referring to FIG. 6D, the reference electrode 150 is formed by depositing a metal film such as platinum (Pt), palladium (Pd), iridium (Ir), tungsten (W) or gold (Au) or a conductive metal oxide on the second insulation film 140 through a deposition process such as sputtering deposition, electronic beam deposition or thermal deposition, and by depositing an oxide material such as $Ag_2SO_4$, $Na_2Ti_6O_{13}$—$TiO_2$, $Li_2TiO_3$—$TiO_2$, $LiMn_2O_4$, $LiCoO_2$—$Co_3O_4$, or $Na_2ZrO_3$—$ZrO_3$ thereon through a deposition process such as thermal deposition, sputtering, screen printing, a sol-gel process, chemical vapor deposition, or inkjet printing. Thereafter, the reference electrode 150 is patterned such that the reference electrode 150 is located at an upper central region of the second insulation film 140.

Figure 6E:
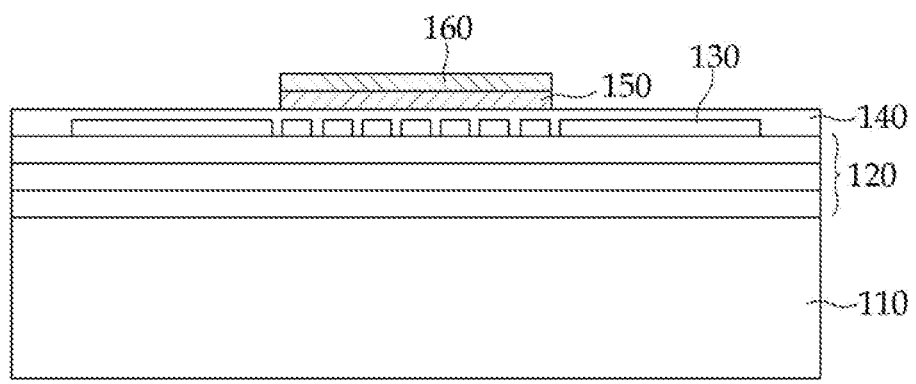

Referring to FIG. 6E, the solid electrolyte 160 such as yttria stabilized zirconia (YSZ), $K_2CO_3$, NASICON ($Na_{1+x}Zr_2Si_xP_{3-x}O_{12}$), $\beta$-$Al_2O_3$($Na_2O.11Al_2O_3$), $Li_3PO_4$, LISICON($Li_{2+2x}Zn_{1-x}GeO_4$), lithium phosphorous oxynitride (LIPON), $Li_2CO_3$—MgO, $Li_2SO_4$, $Li_4SiO_4$, $Li_{14}ZnGe_4O_{16}$, $\gamma$-$Li_{3.6}Ge_{0.6}V_{0.4}O_4$, $Li_3N$, Li-$\beta$-alumina $Li_{1-x}Ti_{2-x}Mx(PO_4)_3$(M=Al, Sc, Y or La), LGPS ($Li_2GeP_2S_{12}$) and $Li_xLa_{(2-x)/3}TiO_3$ is deposited on the reference electrode 150 by using a metal mask or directly at a desired portion through a deposition process such as thermal deposition, sputtering, screen printing, a sol-gel process, chemical vapor deposition, atomic layer deposition and inkjet printing.

Figure 6F:
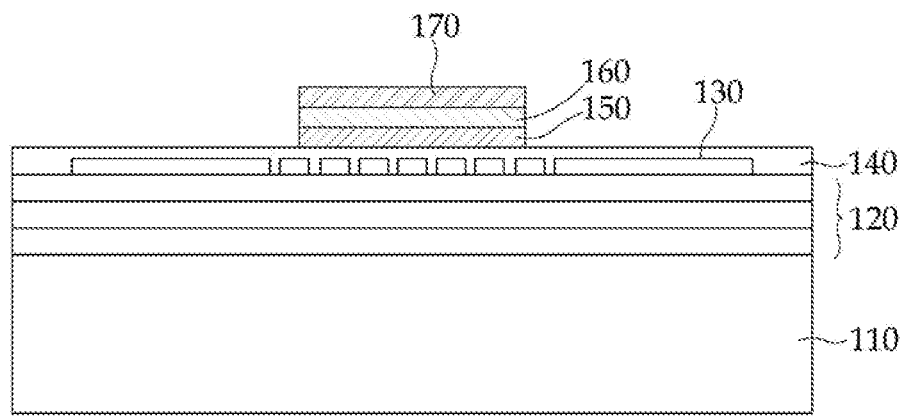

Referring to FIG. 6F, the detection electrode 170 is formed by depositing a metal film such as platinum (Pt), palladium (Pd), iridium (Ir), tungsten (W) or gold (Au) or a conductive metal oxide on the solid electrolyte 160 by using a metal mask or only directly at a desired portion through a deposition process such as sputtering deposition, electronic deposition, chemical vapor deposition, thermal deposition, or inkjet printing and by depositing an oxide material such as $Na_2CO_3$ or mixed $Na_2CO_3$($Na_2CO_3$—$BaCO_3$, $Na_2CO_3$—$Li_2CO_3$, $Li_2CO_3$—$BaCO_3$, $Li_2CO_3$—$CaCO_3$ and the like), $Li_2CO_3$, or mixed $Li_2CO_3$($Li_2CO_3$—$BaCO_3$, $Li_2CO_3$—$SrCO_3$ and $Li_2CO_3$—$CaCO_3$ and the like) or the like thereon through thermal deposition, sputtering, screen printing, a sol-gel process, chemical vapor deposition, atomic layer deposition, inkjet printing or the like.

Figure 6G:
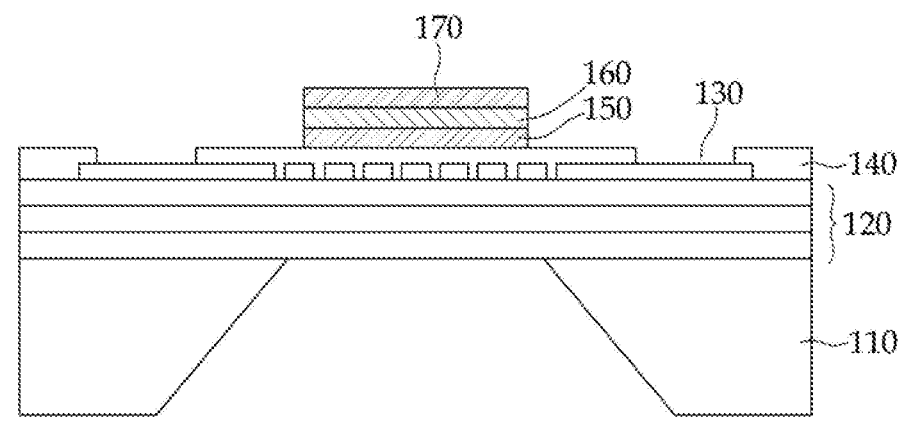

Referring to FIG. 6G, in order to thermally isolate the first insulation film 120 and the heat emitting resistance body 130, a lower central region of the substrate 110 is etched by a predetermined thickness through an etching process such as drying etching using $XeF_2$ or deep reactive ion etching (DRIE) or wet etching using KOH or TMAH. At the same time, the second insulation film 140 may be etched such that a portion of the heat emitting resistance body 130 is exposed. Thus, the heat emitting resistance body 130 may be connected to an external circuit through a heater electrode pad (not shown) and a bonding wire (not shown).

While the substrate etching process is performed after the material depositing process in the exemplary embodiment of the present disclosure, the order of the material deposition process and the substrate etching process may be reversed according to the deposition methods for the reference electrode, the solid electrolyte and the detection electrode. For example, when a detection material deposition method, such as screen printing, where a pressure is applied to a substrate, is used, an MEMS electrochemical gas sensor is manufactured by performing a material deposition process first and then etching the substrate, whereas when a detection material deposition method, such as a sol-gel process, inkjet printing, sputtering deposition, and chemical vapor deposition, where a pressure is not applied to a substrate, is used, a substrate etching process may be performed first and then a material deposition process may be performed later.

The above-configured MEMS electrochemical gas sensors according to the exemplary embodiments of the present disclosure can realize an integration of a detection signal processing/transmitting circuit based on a semiconductor process while minimizing power consumption, can be mass produced, and can be equipped with various functions.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A MEMS electrochemical gas sensor, comprising:
   a substrate;
   a first insulation film disposed over the substrate;
   a heat emitting resistance body disposed over the first insulation film;
   a second insulation film disposed over the heat emitting resistance body;
   a reference electrode disposed over a central region of the second insulation film;
   a solid electrolyte disposed over the reference electrode; and
   a detection electrode disposed over the solid electrolyte,
   wherein the second insulation film exposes a portion of the heat emitting resistance body for coupling the heat emitting resistance body to an external circuit through the exposed portion, and
   wherein an upper central region of the substrate under the reference electrode and the detection electrode is etched by a predetermined thickness to thermally isolate the reference electrode, the detection electrode, and a portion of the heat emitting resistance body under the reference electrode from the substrate.

2. The MEMS electrochemical gas sensor of claim 1, wherein the substrate is a silicon substrate or a substrate doped with any one of aluminum oxide (Al2O3), magnesium oxide (MgO), quartz, gallium-nitrogen (GaN) and gallium-arsenic (GaAs).

3. The MEMS electrochemical gas sensor of claim 1, wherein the first insulation film and the second insulation film include a single or plurality of silicon oxide films or silicon nitride films.

4. The MEMS electrochemical gas sensor of claim 1, wherein the heat emitting resistance body includes a metal including at least one of platinum (Pt), palladium (Pd), iridium (Ir), tungsten (W), gold (Au), silicon and a conductive metal oxide.

5. The MEMS electrochemical gas sensor of claim 1, further comprising:
   an attachment layer disposed between the first insulation film and the heat emitting resistance body and containing chrome (Cr) or titanium (Ti).

6. The MEMS electrochemical gas sensor of claim 1, wherein the reference electrode includes a metal including at least one of platinum (Pt), palladium (Pd), iridium (Ir), tungsten (W), gold (Au) and an oxide material including at least one of Ag2SO4, Na2Ti6O13-TiO2, Li2TiO3-TiO2, LiMn2O4, LiCoO2-Co3O4 and Na2ZrO3-ZrO3.

7. The MEMS electrochemical gas sensor of claim 1, wherein the solid electrolyte includes at least one of yttria stabilized zirconia (YSZ), K2CO3, NASICON(Na1+xZr2SixP3-xO12), β-Al2O3(Na$_2$O.11Al2O3), Li3PO4, LISICON(Li2+2xZn1-xGeO4), lithium phosphorous oxynitride (LIPON), Li2CO3-MgO, Li2SO4, Li4SiO4, Li14ZnGe4O16, γ-Li3.6Ge0.6V0.4O4, Li3N, Li-β-alumina, Li1+xTi2-xMx(PO4)3(M=Al, Sc, Y or La), LGPS (Li2GeP2S12) and LixLa(2−x)/3TiO3.

8. The MEMS electrochemical gas sensor of claim 1, wherein the detection electrode includes a metal including at least one of platinum (Pt), palladium (Pd), iridium (Ir), tungsten (W), gold (Au) and an oxide material including at least one of Na2CO3, mixed Na2CO3(Na2CO3-BaCO3, Na2CO3-Li2CO3, Li2CO3-BaCO3 and Li2CO3-CaCO3), Li2CO3 and mixed Li2CO3(Li2CO3-BaCO3, Li2CO3-SrCO3 and Li2CO3-CaCO3).

9. The MEMS electrochemical gas sensor of claim 1, wherein the reference electrode and the detection electrode have an interdigital shape, a hollow box shape, a box shape, or a combination thereof.

10. A MEMS electrochemical gas sensor, comprising:
    a substrate;
    a first insulation film disposed over the substrate;
    a heat emitting resistance body disposed over the first insulation film;
    a second insulation film disposed over the heat emitting resistance body;
    a solid electrolyte disposed over a central region of the second insulation film;
    a reference electrode disposed at a first side of an upper portion of the solid electrolyte; and
    a detection electrode disposed at a second side of the upper portion of the solid electrolyte opposite to the first side,
    wherein the second insulation film exposes a portion of the heat emitting resistance body for coupling the heat emitting resistance body to an external circuit through the exposed portion, and
    wherein an upper central region of the substrate under the reference electrode and the detection electrode is etched by a predetermined thickness to thermally isolate the reference electrode, the detection electrode, and a portion of the heat emitting resistance body under the reference electrode and the detection electrode from the substrate.

11. The MEMS electrochemical gas sensor of claim 10, wherein the reference electrode and the detection electrode have an interdigital shape, a hollow box shape, a box shape, or a combination thereof.

12. The MEMS electrochemical gas sensor of claim 1, wherein the detection electrode is coupled to a bonding wire to transfer signals to the external circuit.

13. The MEMS electrochemical gas sensor of claim 10, wherein the detection electrode is coupled to a bonding wire to transfer signals to the external circuit.

* * * * *